(12) United States Patent
Zimmermann et al.

(10) Patent No.: US 7,415,299 B2
(45) Date of Patent: Aug. 19, 2008

(54) MONITORING METHOD AND/OR APPARATUS

(75) Inventors: Stefan Zimmermann, Berkeley, CA (US); Boris Stoeber, Berkeley, CA (US); Dorian Liepmann, Lafayette, CA (US); Albert Pisano, Danville, CA (US)

(73) Assignee: The Regents of the University of California, Oakland, CA (US)

( * ) Notice: Subject to any disclaimer, the term of this patent is extended or adjusted under 35 U.S.C. 154(b) by 361 days.

(21) Appl. No.: 10/828,510

(22) Filed: Apr. 19, 2004

(65) Prior Publication Data

US 2006/0211933 A1 Sep. 21, 2006

Related U.S. Application Data

(60) Provisional application No. 60/464,221, filed on Apr. 18, 2003.

(51) Int. Cl.
 *A61B 5/05* (2006.01)
(52) U.S. Cl. ............... 600/345; 600/365; 604/4.01; 210/321.75
(58) Field of Classification Search ............... 600/345; 604/29, 207, 210, 4.01, 5.01, 5.04, 6.09; 210/195.2, 321.75–321.8, 348, 500.1, 500.21
See application file for complete search history.

(56) References Cited

U.S. PATENT DOCUMENTS

| | | | | |
|---|---|---|---|---|
| 5,097,834 A | * | 3/1992 | Skrabal | 600/366 |
| 5,243,982 A | * | 9/1993 | Mostl et al. | 600/316 |
| 6,091,976 A | | 7/2000 | Pfeiffer et al. | |
| 6,406,638 B1 | | 6/2002 | Stoeber et al. | |
| 2001/0016682 A1 | * | 8/2001 | Berner et al. | 600/345 |
| 2002/0006355 A1 | * | 1/2002 | Whitson | 422/56 |
| 2002/0082543 A1 | * | 6/2002 | Park et al. | 604/21 |
| 2003/0135158 A1 | * | 7/2003 | Gonnelli | 604/140 |
| 2003/0135201 A1 | * | 7/2003 | Gonnelli | 604/890.1 |
| 2003/0143746 A1 | * | 7/2003 | Sage | 436/8 |

OTHER PUBLICATIONS

Baker et al. (1999) "Fluid mechanics analysis of a spring-loaded jet injector," *IEEE Transactions on Biomedical Engineering*, 46 (2), Feb. 1999, pp. 235-242.
Cheyne et al. (2002) "Making 'sense' of diabetes: using a continuous glucose sensor in clinical practice," *Diabetes Metab Res Rev*, 18 (Suppl. 1) pp. 543-548.
Freckmann et al. (2001) "Recent advances in continuous glucose monitoring." *Exp Clin Endocrinol Diabetes*, 109, Suppl 2: S347-S357.
Freckmann et al. (2002) "Measurement of the Postprandial Physiological Time Lag Between Whole Blood- and Subcutaneous Tissue Glucose Traces Following Meals in Type 1 Diabetic Patients," Poster-No. 553; *PS 37 Insulin Action, 38th EASD Annual Meeting*, Budapest, Hungary, Sep. 1-5, 2002.

(Continued)

*Primary Examiner*—Robert L. Nasser, Jr.
*Assistant Examiner*—Karen E Toth
(74) *Attorney, Agent, or Firm*—Quine Intellectual Property Law Group, P.C.; Stephen J. LeBlank, Esq.

(57) ABSTRACT

A method and apparatus for substance monitoring. One application is an easy to handle continuous glucose monitor using a group of hollow out-of-plane silicon microneedles to sample substances in interstitial fluid from the epidermal skin layer. The glucose of the interstitial fluid permeates a dialysis membrane and reaches a sensor. Using MEMS technology, for example, allows well-established batch fabrication at low cost.

5 Claims, 15 Drawing Sheets

OTHER PUBLICATIONS

Hoss et al. (2001) "A Novel Method for Continuous Online Glucose Monitoring in Humans: The Comparative Microdialysis Technique," *Diabetes Technology & Therapeutics*, vol. 3, No. 2, pp. 237-243.

Ichimura (1984) "A Convenient Photochemical Method to Immobilize Enzymes," *Journal of Polymer science: Polymer Chemistry Edition*, John Wiley & Sons, vol. 22, pp. 2817-2828, (1984).

Kalatz et al. (2000) "Feedback-Regulation of Subcutaneous Insulin Infusion by Continuous Subcutaneous Glucose Measurement," *Acta Diabetol* 37:164 (abstract).

Kendall et al. (2000) "Transdermal ballistic delivery of Micro-particles: Investigation into skin penetration," *Proceedings of the 22nd Annual EMBS International Conference*, Jul. 23-28, Chicago, IL, USA, pp. 1621-1624, 2000.

Lee et al. (2000) "In vivo transdermal delivery using a shock tube," *Shock Waves*, 10, pp. 307-311, 2000.

Lopez (2002) "In situ fabricated microdialysis microchannels with biofouling prevention employing electrical methods," Thesis Proposal Draft, The Robotics Institute, Carnegie Mellon University, Jul. 2002.

Nguyen et al. (2002) "MEMS-Micropumps: A Review," *Journal of Fluids Engineering*, Transactions of the ASME, vol. 124, pp. 384-392.

Paranjape et al. (2002) "Dermal thermo-poration with a PDMS-based patch for transdermal biomolecular detection," *Technical Digest of the Solid-State Sensor, Actuator, and Microsystems Workshop 2002*, Hilton Head Island, SC, USA, Jun. 2-6, pp. 73-76, 2002.

Pfeiffer et al. (2002) "A Novell Selfcalibrating Method for Continuous Online Determination of Subcutaneous Tissue Glucose, based on the Microdialysis Technique," Poster #98, *Second Annual Diabetes Technology Meeting*, Oct. 31-Nov. 2, 2002, Atlanta, Georgia USA.

Pfeiffer et al. (2002) "A Mathematical Index of Short Term Time Courses of Continuous Glucose Traces," Poster-No. 861; *PS 68 Alternative Site Glucose Testing, 38th EASD Annual Meeting*, Budapest, Hungary, Sep. 1-5, 2002.

Pfeiffer et al. (2002) "Increasing the linearity of enzyme-bsed amperometric glucose sensors by adding perfluorcarbon emulsions to the reaction," Poster #99, *Second Annual Diabetes Technology Meeting*, Oct. 31-Nov. 2, 2002, Atlanta, Georgia, USA.

Pitzer et al. (2001) "Detection of Hypoglycemia with the GlucoWatch Biographer", *Diabetes Care*, vol. 24, No. 5, pp. 881-885.

Xinglong et al. (2001) "Particle acceleration for delivery deoxyribonucleic acid vaccine into skin in vivo," *Review of Scientific Instruments*, 72 (8), pp. 3390-3395, 2001.

Zahn (2001) "Microfabricated Microneedles for Minimally Invasive Drug Delivery, Sampling and Analysis," Dissertation, Ph.D. Engineering-Bioengineering, UC Berkeley and UC San Francisco, Spring 2001.

Zahn et al. (2000) "Microfabricated Microdialysis Microneedles for Continuous Medical Monitoring," *1st Annual International IEEE-EMBS Special Topic Conference on Microtechnologies in Medicine & Biology*, Oct. 12-14, 2000, Lyon, France.

Zahn et al. (2001) "An Integrated Microfluidic Device for the Continuous Sampling and Analysis of Biological Fluids," *Proceedings of 2001 ASME International Mechanical Engineering Congress and Exposition*, Nov. 11-16, New York, NY, USA.

Zahn et al. (2001) "Continuous on-chip micropumping through a microneedle," *14th Annual IEEE International MEMS-01 Conference*, pp. 503-506.

\* cited by examiner

Photo of the bonded wafers.

Photo of a glucose sensor integrated in a flow channel.

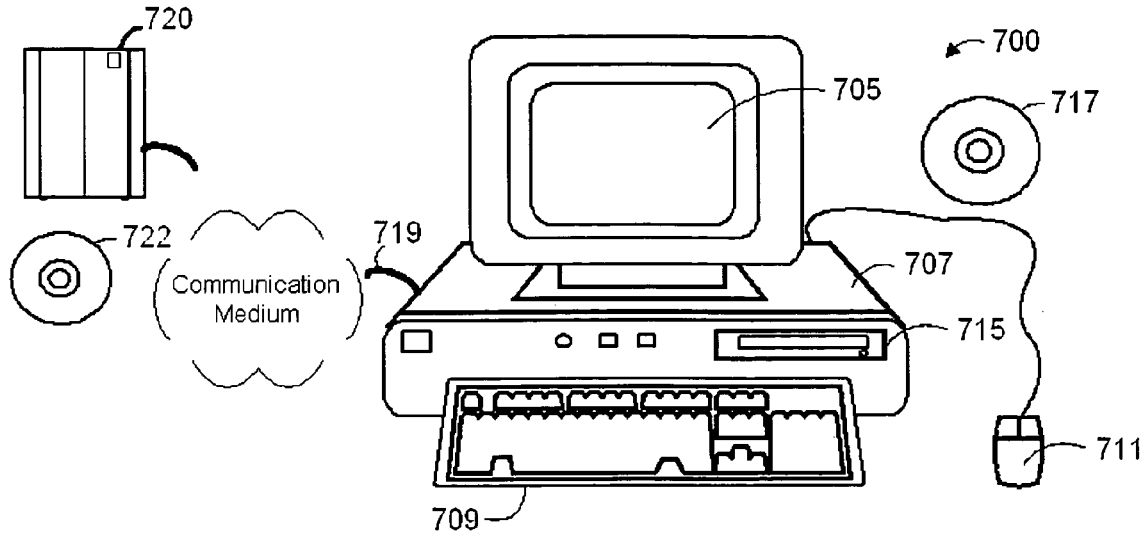

*FIG. 18*

| Disease Classification | Disease |
|---|---|
| Cardiovascular Disease | Atherosclerosis; Unstable angina; Myocardial Infarction; Restenosis after angioplasty or other percutaneous intervention; Congestive Heart Failure; Myocarditis; Endocarditis; Endothelial Dysfunction; Cardiomyopathy |
| Endocrine Disease | Diabetes Mellitus I and II; Thyroiditis; Addisson's Disease |
| Infectious Disease | Hepatitis A, B, C, D, E; Malaria; Tuberculosis; HIV; Pneumocystis Carinii; Giardia; Toxoplasmosis; Lyme Disease; Rocky Mountain Spotted Fever; Cytomegalovirus; Epstein Barr Virus; Herpes Simplex Virus; Clostridium Dificile Colitis; Meningitis (all organisms); Pneumonia (all organisms); Urinary Tract Infection (all organisms); Infectious Diarrhea (all organisms) |
| Angiogenesis | Pathologic angiogenesis; Physiologic angiogenesis; Treatment induced angiogenesis |
| Inflammatory/Rheumatic Disease | Rheumatoid Arthritis; Systemic Lupus Erythematosis; Sjogrens Disease; CREST syndrome; Scleroderma; Ankylosing Spondylitis; Crohn's; Ulcerative Colitis; Primary Sclerosing Cholangitis; Appendicitis; Diverticulitis; Primary Biliary Sclerosis; Wegener's Granulomatosis; Polyarteritis nodosa; Whipple's Disease; Psoriasis; Microscopic Polyanngiitis; Takayasu's Disease; Kawasaki's Disease; Autoimmune hepatitis; Asthma; Churg-Strauss Disease; Beurger's Disease; Raynaud's Disease; Cholecystitis; Sarcoidosis; Asbestosis; Pneumoconioses |
| Transplant Rejection | Heart; Lung; Liver; Pancreas; Bowel; Bone Marrow; Stem Cell; Graft versus host disease; Transplant vasculopathy |
| Leukemia and Lymphoma | |

*FIG. 19. (TABLE 1)*

MONITORING METHOD AND/OR APPARATUS

CROSS REFERENCE TO RELATED APPLICATIONS

This application claims priority from provisional patent application 60/464,221 filed 18 Apr. 2003 and incorporated herein by reference.

The Invention was made with government support under Grant (Contract) No. F30602-00-2-0566 awarded by the Department of Defense. The Government has certain rights to this invention.

COPYRIGHT NOTICE

Pursuant to 37 C.F.R. 1.71(e), Applicants note that a portion of this disclosure contains material that is subject to copyright protection (such as, but not limited to, source code listings, screen shots, user interfaces, or user instructions, or any other aspects of this submission for which copyright protection is or may be available in any jurisdiction.). The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

Currently proposed systems for monitoring substances of interest, such as glucose, using small sampling and monitoring devices have a number of difficulties. For example, a microdialysis probe discussed for glucose monitoring in U.S. Pat. No. 6,091,976, Jul. 18, 2000 (M. Pfeiffer and U. Hoss) is a needle-type probe with dialysis fluid flowing in and out of the probe. The probe is inserted at a length of several millimeters underneath the skin at a shallow angle so that the probe stays in the epidermal tissue. A dialysis membrane separates the probe interior from the interstitial fluid surrounding the probe. This membrane allows diffusion of substances such as glucose from the interstitial fluid into the dialysis fluid flowing in and out of the probe. The interstitial fluid is not extracted. The dialysis fluid is then pumped to a sensor placed downstream where the glucose level of the dialysis fluid is determined. The glucose concentration of the dialysis fluid has been found to correlate with the glucose level in the interstitial fluid.

Despite the name microdialysis probe in this instance, the probe dimensions are in the millimeter range. In these proposals, the reason for using such a long probe is that the area of the dialysis membrane generally defines the amount of glucose diffusing into the dialysis fluid during a given amount of time. Generally, the detection limit of practicable glucose sensors requires a certain amount of glucose in the dialysis fluid to get reliable sensor signals. The required membrane area necessary for sufficient glucose diffusion and high sensor signals is several square millimeters and this membrane generally defines the size of the probe, which explains the large dimensions of the dialysis probes and/or needles in these discussions.

A disadvantage of using a large "micro" dialysis probe is a generally painful insertion procedure that generally requires trained personnel to implant the probe underneath the skin. Thus, present microdialysis proposals do not easily allow for painless everyday usage.

According to the World Health Organization the per capita diabetes rate in the US increased from 5.2% (world: 2.4%) in 1995 to 6.0% (2.9%) in 2000, and it is expected to reach 8.4% (4.5%) in 2030. While diabetes is the leading cause of blindness, kidney failure and non-traumatic amputation of the lower limp, other severe complications associated with hyperglycemia (high glucose levels) and hypoglycemia (low glucose levels) are nerve damage, heart disease, coma and brain damage. The traditional fingerstick test typically takes periodic samples, but this monitoring can miss periods of hyperglycemia and hypoglycemia, especially during sleep. This health risk can be avoided using a continuous glucose monitor.

Currently available continuous glucose monitoring systems include the Cygnus GlucoWatch® and the Minimed CGMS™. However, it is believed that these systems cannot provide an accurate everyday glucose level control and still require periodic fingerstick tests for sensor recalibration. The GlucoWatch® is easy to use but it relies on reverse iontophoretic interstitial fluid sampling through the skin, which is affected by fluctuating skin permeability as described in K. R. Pitzer, S. Desai, T. Dunn, S. Edelman, Y. Jayalakshmi, J. Kennedy, J. A. Tamada, R. O. Potts, Detection of Hypoglycemia with the GlucoWatch Biographer, Diabetes Care, Vol. 24, No. 5, 2001

The CGMS™ is generally not designed for daily usage; it requires trained personnel to insert the sensor under the skin, as described in E. Cheyne, D. Kerr, Making 'sense' of diabetes: using a continuous glucose sensor in clinical practice, Diabetes Metab Res Rev, 18 (Suppl. 1), 2002.

While frequent and long periods of hyperglycemic blood glucose levels can account for many long-term complications, hypoglycemia can cause sudden coma and brain damage. Periodic fingerstick tests often fail to detect all hypoglycemic and hyperglycemic events since glucose levels can change rapidly. In particular, nocturnal hypoglycemia often remains undetected.

SUMMARY

The present invention, in specific embodiments, involves novels methods for minimally invasive monitoring. In further embodiments, the invention provides a device and/or method for detecting and or monitoring substances of interest, particular substances in biological research and/or clinical settings. In further embodiments, the invention provides a device and/or method using dialysis and out-of-plane microneedles to provide an improved sensor.

In more specific embodiments, the invention involves a method and/or apparatus for monitoring of substances in interstitial fluid under the skin of a human or animal or under the outer layer of a plant using out-of-plane microneedles. For humans and animals, this can allow painless everyday usage.

In specific embodiments, the invention can be distinguished from proposals describing generally a single microdialysis probe or needle. In the present invention, it is not necessary to insert a dialysis probe or needle underneath the skin. In specific embodiments of the invention, the dialysis portion of the device remains outside of the body, even in a very small monitoring system.

In other embodiments the invention relates generally to a method and apparatus for continuous monitoring of compounds in the epidermal interstitial fluid. As a specific example, the invention relates to a minimally invasive method for sampling compounds from the epidermal interstitial fluid using hollow out-of-plane microneedles and the apparatus for sampling and analyzing these compounds. A particular application of this invention is to continuously monitor the epidermal interstitial fluid glucose level.

In further specific embodiments, the invention involves an array (used herein to indicate any type of grouping) of out-of-plane microneedles that vertically penetrate a skin or other surface. In specific applications, the microneedles are approximately 200 μm long, which, for example, is sufficient to reach the epidermal interstitial fluid in humans. In further embodiments, the invention involves microneedles that are pre-filled with a liquid, such as a buffer solution, resulting in a liquid-liquid interface between the liquid inside the needle and the interstitial fluid once the needle is inserted. Substances from the interstitial fluid such as glucose can diffuse into the lumens of the out-of-plane microneedles. In further embodiments, a dialysis membrane is placed on an opposite side of a substrate from the microneedles. Thus, the membrane separates the needle lumens from the dialysis fluid, which is pumped past the membrane to the glucose sensor. The amount of glucose diffusing through the out-of-plane microneedles, through the membrane and into the dialysis fluid is generally defined by the total area where diffusion can take place. This area is defined by the total cross section of all needle lumens.

In further example embodiments, a group of microneedles in included in a system along with a system and/or method for automatic calibration. Automatic calibration allows the system to provide reliable monitoring results without the need for additional calibration methods, such as a needle-stick test. According to specific embodiments of the invention, the dialysis system use in combination with the out-of-plane microneedles facilitates sensor recalibration.

The present invention in specific embodiments provides a disposable sensor system that is minimally invasive and provides accurate sensor readings and painless and easy sensor application. An example of such a system system consists of hollow out-of-plane microneedles to sample glucose from the interstitial fluid of the epidermis, an integrated dialysis membrane and an integrated electrochemical enzyme-based flow-through glucose sensor.

In a further and very specific example embodiment, an array of between about 600 to 1500 microneedles is placed on an approximately 8 mm×8 mm substrate. One advantage of using an array of out-of-plane microneedles is that the resulting membrane area is large enough for effective diffusion but the insertion of a number of out-of-plane microneedles is painless since the needles are in fact very small, actually in the micro-meter range. In addition the needle array is easy to apply by fixing (e.g., by taping) or pressing the device onto the skin rather the inserting a dialysis probe at a shallow angle several millimeter long underneath the skin. According to specific embodiments of the invention, a monitoring device using microneedles can be applied to the skin and effectively sample substances in interstitial without penetrating deeply enough to impact nerve endings.

While example detectors according to specific embodiments of the present invention are described herein as used for performing a biological assay, it will be understood to those of skill in the art that a detector according to specific embodiments of the present invention can be used in a variety of applications for detecting substances of interests. These applications include, but are not limited to: detecting contaminants in foodstuffs; detecting ripeness and/or the presence of sugars in plants or plant parts; detecting the presence of a desired substance (such as petroleum components) in an exploration operation; insuring the presence of desired elements in a manufacturing product, etc.

The invention and various specific aspects and embodiments will be better understood with reference to drawings and detailed descriptions provided in this submission. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents.

Furthermore, it is well known in the art that systems and methods such as described herein can include a variety of different components and different functions in a modular fashion. Different embodiments of the invention can include different mixtures of elements and functions and may group various functions as parts of various elements. For purposes of clarity, the invention is described in terms of systems that include different innovative components and innovative combinations of innovative components and known components. No inference should be taken to limit the invention to combinations containing all of the innovative components listed in any illustrative embodiment in this specification.

In some of the drawings and detailed descriptions below, the present invention is described including various parameters of dimension and/or other parameters. These should be understood as illustrating specific and possible preferred embodiments, but are not intended to limit the invention. Many devices and/or methods have variations in one or more of the detailed parameters described herein will be apparent to persons of skill in the art having the benefit of the teachings provided herein and these variations are included as part of the present invention.

All references, publications, patents, and patent applications cited and/or provided with this submission are hereby incorporated by reference in their entirety for all purposes.

BRIEF DESCRIPTION OF THE DRAWINGS

FIG. 18 is a block diagram showing a representative example logic device in which various aspects of the present invention may be embodied.

FIG. 19 (Table 1) illustrates an example of diseases, conditions, or statuses for which substances of interest can evaluated according to specific embodiments of the present invention.

DESCRIPTION OF SPECIFIC EMBODIMENTS

1. Definitions

Figure 1:
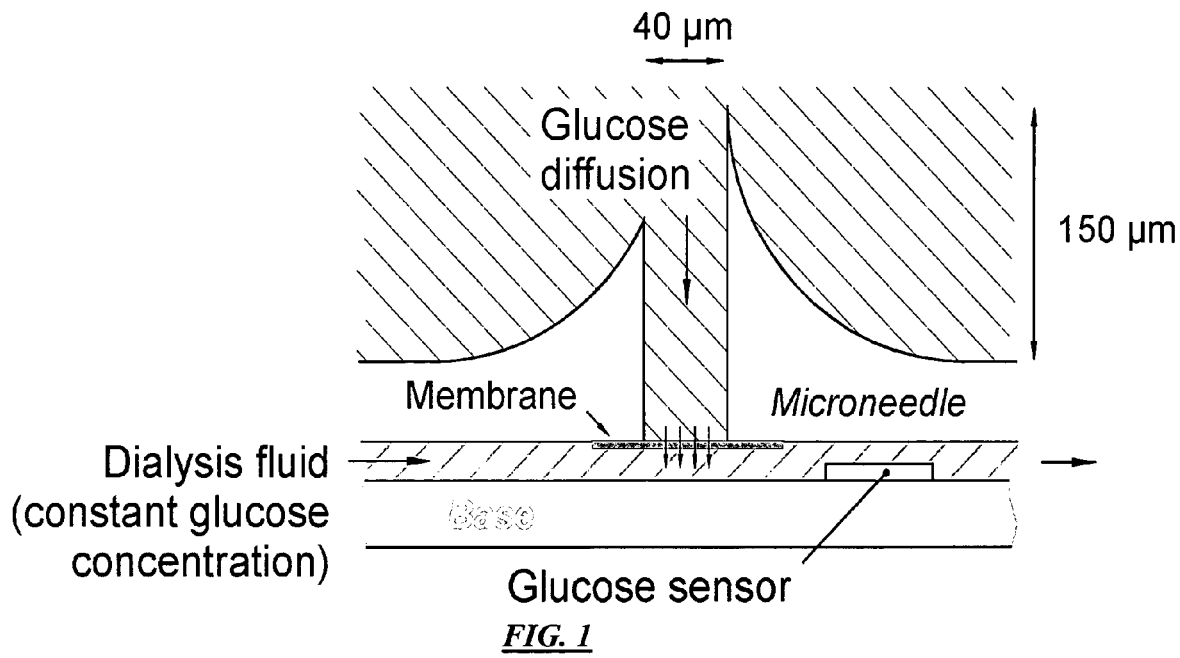
FIG. 1 is a schematic diagram of an example microneedle-based continuous monitor wherein microneedle lumens are filled with interstitial fluid by capillary action and a substance of interest diffuses through the integrated dialysis membrane into dialysis fluid that is pumped past an integrated enzyme-based flow-through sensor according to specific embodiments of the invention.

The following definitions may be used to assist in understanding this submission. These terms, as well as terms as understood in the art should be used as a guide in understanding descriptions provided herein.

A "substrate" is a, preferably solid, material suitable for the attachment of one or more molecules. Substrates can be formed of materials including, but not limited to glass, plastic, silicon, germanium, minerals (e.g. quartz), semiconducting materials (e.g. silicon, germanium, etc.), ceramics, metals, etc.

2. Overview of the Invention

According to specific embodiments, the present invention involves methods, devices, and systems that enable a new approach to monitoring substances of interest from within an environment (such as a plant or animal) by using out-of-plane microneedles and a sensing method that is substantially external to the environment in which a substance is being monitored. A primary application is continuous glucose monitoring in humans, though other applications are contemplated.

Integrated systems and/or methods of the invention generally comprise an array of out-of-plane microneedles that are inserted into an area to be sensed (such as skin), and integrated into the non-inserted side of the microneedles one or more sensing components. The microneedles can be of various configurations, examples of which are described herein. The sensing components in their most simple state can include a prefilled buffer reservoir with chemical and/or electrical sensor components. Other systems can include dialysis elements, electronic controls, small scale or microfluidic channels, pumps, and systems, dialysis components and/or calibration components. A number of example configurations of such integrated systems are described in detail below.

The invention is also involved with a number of novel techniques and/or devices that enable or improve such monitoring systems in particular embodiments. These techniques and/or devices have applications and uses in different systems than the examples given here, as will be understood by those of skill in the art from these teachings and in some cases are independently novel.

3. Example System Configurations

To provide different contexts for understanding embodiments of the present invention, various example embodiment of sensing systems or portions thereof according to specific embodiments of the invention are illustrated in FIG. 1 through FIG. 5

In each case, these figures schematically represent the combination of out-of-plane microneedle arrays with other components to form a microneedle array detection system. Note that, in each of these illustrations, the one to three microneedles illustrated should be understood to represent an array of generally tens, hundreds, or a thousand or more microneedles as illustrated below. In some embodiments, a large set, up to all available microneedles, may be integrated with a single detection system at the base of the needle. In other systems, two or more separate detection systems can be integrated at the base of a single microneedle array, either to provide different sensing, for ease of use or manufacturing, for staged use, or to provide a control system.

Dialysis

FIG. 1, FIG. 3, FIG. 4, and FIG. 5 each illustrate different embodiments of a sensor system that includes a dialysis membrane to separate the sensing area from the sample area. This is a presently preferred embodiment. Dialysis is a well known technique for using a selectively permeable membrane between two fluids to allow diffusion of a desired substance while preventing diffusion of other substances. One example membrane that can be used in systems according to specific embodiments of the invention is an integrated porous polysilicon dialysis membrane, as will be understood in the art. Other example membrane technology will be understood from the description herein and cited references. In systems according to specific embodiments of the invention, the dialysis membrane is any membrane or system or structure that allows diffusion of a substance that is intended to be detected and prevents one or more possibly interfering substances.

Diffusion

Figure 2:
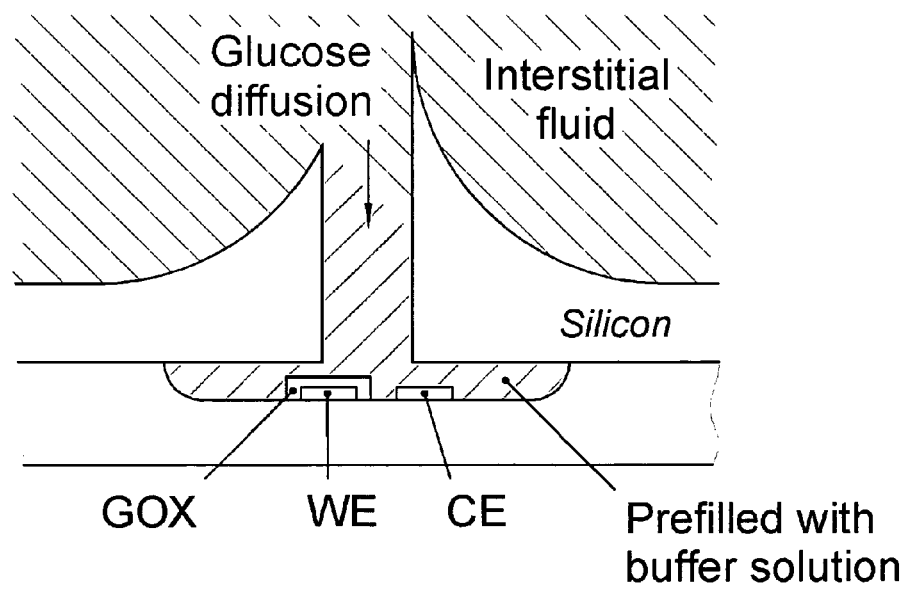
FIG. 2 is a schematic diagram of an example simplified microneedle-based monitor wherein a pre-filled system allows glucose diffusion through the microneedles to an integrated two-electrode enzyme-based sensor according to specific embodiments of the invention.

FIG. 2 is a schematic diagram of an example simplified microneedle-based monitor wherein a pre-filled system allows glucose diffusion through the microneedles to an integrated two-electrode enzyme-based sensor according to specific embodiments of the invention. While this system may not have the lifetime or reliability of the dialysis-based systems in human applications, it has proven valuable as a prototyping design and has applications where ease of manufacturing and/or reduced cost are primary considerations or where the sensor is used in applications that do not involve the presence of proteins or other compounds that can contaminate the sensing components.

4. Operation Examples

As an example of operation, in these detectors, glucose or another substance of interest that is present in blood or interstitial fluid diffuses into the microneedles. This transport may be facilitated by prefilling the microneedles with a substance to aid diffusion (e.g., a buffer fluid or gel) to prevent air trapped in the needle lumen from blocking fluidic flow or diffusion. With the lumen in contact with the interstitial fluid, substances of interest can come in contact with one or more sensors, such as chemical, electrical, electrochemical, optical, temperature, etc. sensors. In the example systems, example sensors include the WE, CE and/or RE electrodes shown in FIG. 1, the integrated sensor components shown in FIG. 2. Catalysts or reagents can also be included depending on the type of sensing assay being used (e.g., the GOX regions shown in the figures).

Operation Example Details

A sensor system according to specific embodiments of the invention can have a number of components depending on the particular type of sensor used. Systems including dialysis include a dialysis barrier and can include a dialysis fluid reservoir, fluidic channels, micropumps and values as shown. Systems including a calibration system can include a calibration fluid reservoir, fluidic channels, micropumps and values as shown. In some embodiments, calibration fluid is segregated from sample or dialysis fluid by a moveable valve or by a flow restriction valve as shown. In alternative embodiments, calibration can be accomplished by changing the flow rate of dialysis fluid and using that fluid for calibration.

EXAMPLE 1

FIG. 1 is a schematic diagram of an example microneedle-based continuous monitor wherein microneedle lumens are filled with interstitial fluid by capillary action and a substance of interest diffuses through the integrated dialysis membrane into dialysis fluid that is pumped past an integrated enzyme-based flow-through sensor according to specific embodiments of the invention. In this example, an array of hollow out-of-plane microneedles is used to penetrate the skin and to interface with the interstitial fluid. A dialysis membrane separates the interstitial fluid and the dialysis fluid; thus, no interstitial fluid is extracted during operation. Dialysis fluid with a known constant glucose concentration is continuously pumped past the dialysis membrane and an integrated sensor (e.g., for glucose). Glucose diffuses through the microneedles and through the dialysis membrane into or out of the dialysis fluid. The concentration change in dialysis fluid is measured—it depends on the flow rate of the dialysis fluid and the glucose concentration in the interstitial fluid. At high flow rates (recalibrating mode) the amount of glucose diffusing into the dialysis fluid is negligible so that the glucose concentration of the dialysis fluid remains unchanged. Thus, a known concentration is measured and the sensor can be recalibrated. At low flow rates (measuring mode) the concentration in the dialysis fluid changes significantly—the change in glucose concentration corresponds to the glucose concentration in the interstitial fluid.

EXAMPLE 2

Figure 3:
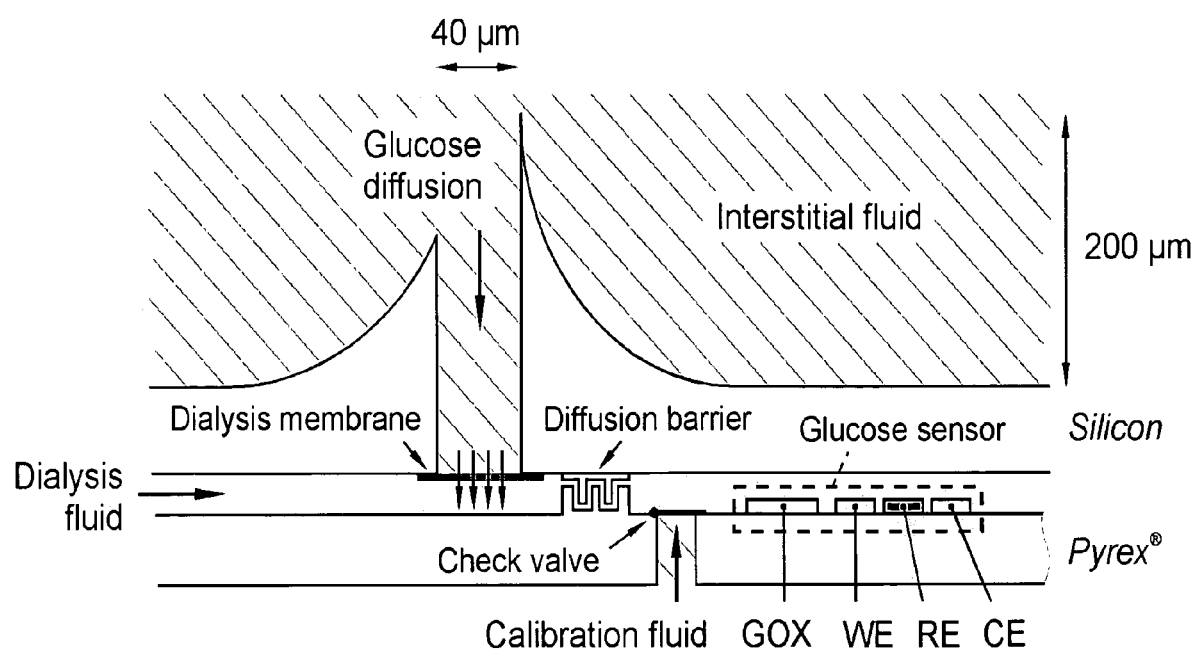
FIG. 3 is a schematic diagram of an example microneedle-based continuous monitor including a separate calibration fluid system according to specific embodiments of the invention.

FIG. 3 is a schematic diagram of an example microneedle-based continuous monitor including a separate calibration fluid system according to specific embodiments of the invention. In this further specific example, operation of the example sensor can be understood as follows. An group of, for example, about 200 μm long hollow out-of-plane microneedles are used to penetrate the topmost layer of the skin, allowing their opening to come in contact with interstitial fluid from the epidermis. Once the microneedles are either filled with interstitial fluid or once sufficient time has elapsed for a substance of interest to diffuse into prefilled needles, the substance of interest (e.g., glucose) diffuses through the dialysis membrane into dialysis fluid, keeping unwanted substances (e.g., larger protein molecules) outside of the dialysis area, thus improving the sensor long-term stability.

Various detection strategies can be used for detecting substances of interest. Different strategies may be employed in different embodiments of the invention. As one example, consider the enzyme-based flow-through glucose sensor shown in FIG. 3. This sensor includes a Pt working electrode (WE), an Ag/AgCl reference electrode (RE) and a Pt counter electrode (CE). The glucose oxidase (GOX) is immobilized upstream from the working electrode inside the flow channel.

In this example system, an integrated diffusion barrier channel prevents glucose diffusion from the calibration fluid into the dialysis fluid during sensor recalibration. Other types of barriers, such as moveable valves, etc., can be used in other embodiments, but a barrier as shown is easy to fabricate and effective in many situations. The diffusion barrier consisting of a long and narrow diffusion path prevents diffusion of glucose from the calibration fluid into the dialysis fluid during sensor recalibration. In the figure, this barrier is shown with the diffusion path oriented vertically in the dialysis fluid channel. While this provides an easy to view illustration, using typical microfabrication techniques, the diffusion barrier will usually more easily be fabricated with the diffusion path oriented horizontally on the substrate and thus the diffusion barrier path shown in FIG. 3 can be understood as a top down view of that portion of the system.

Electrical-Chemical Sensor

As an example of one type of sensor that can be used in a microneedle system according to specific embodiments of the invention, the sensor components shown in FIG. 3 are further described. In the presence of dissolved oxygen, glucose oxidase immobilized inside the channel catalyses the oxidation of glucose to gluconic acid. Hydrogen peroxide is formed as a by-product.

$$\text{Glucose} + O_2 \Rightarrow \text{Gluconic acid} + H_2O_2$$

The hydrogen peroxide is detected downstream using an integrated electrochemical sensor. The working electrode is biased 0.7 V versus the reference electrode. Thus, hydrogen peroxide is oxidized at the working electrode and the resulting electric current is proportional to the glucose concentration inside the dialysis fluid.

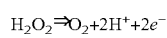

$$H_2O_2 \Rightarrow O_2 + 2H^+ + 2e^-$$

In this example system, an integrated diffusion barrier channel prevents glucose diffusion from the calibration fluid into the dialysis fluid during sensor recalibration. Other types of barriers, such as moveable valves, etc., can be used in other embodiments, but a barrier as shown is easy to fabricate and effective in many situations. The diffusion barrier consisting of a long and narrow diffusion path prevents diffusion of glucose from the calibration fluid into the dialysis fluid during sensor recalibration. In the figure, this barrier is shown with the diffusion path oriented vertically in the dialysis fluid channel. While this provides an easy to view illustration, using typical microfabrication techniques, the diffusion barrier will usually more easily be fabricated with the diffusion path oriented horizontally on the substrate and thus the diffusion barrier path shown in FIG. 3 can be understood as a top down view of that portion of the system.

Since the chlorine ion concentration in biological fluids remains constant at 0.15 mM a simple planar Ag/AgCl electrode can serve as a pseudo reference electrode. For automatic sensor recalibration, reference glucose solution is periodically pumped past the sensor. Thus, no fingerstick tests are required to account for the usual gradual loss of enzyme activity during the sensor operation time.

EXAMPLE 3

Figure 4:
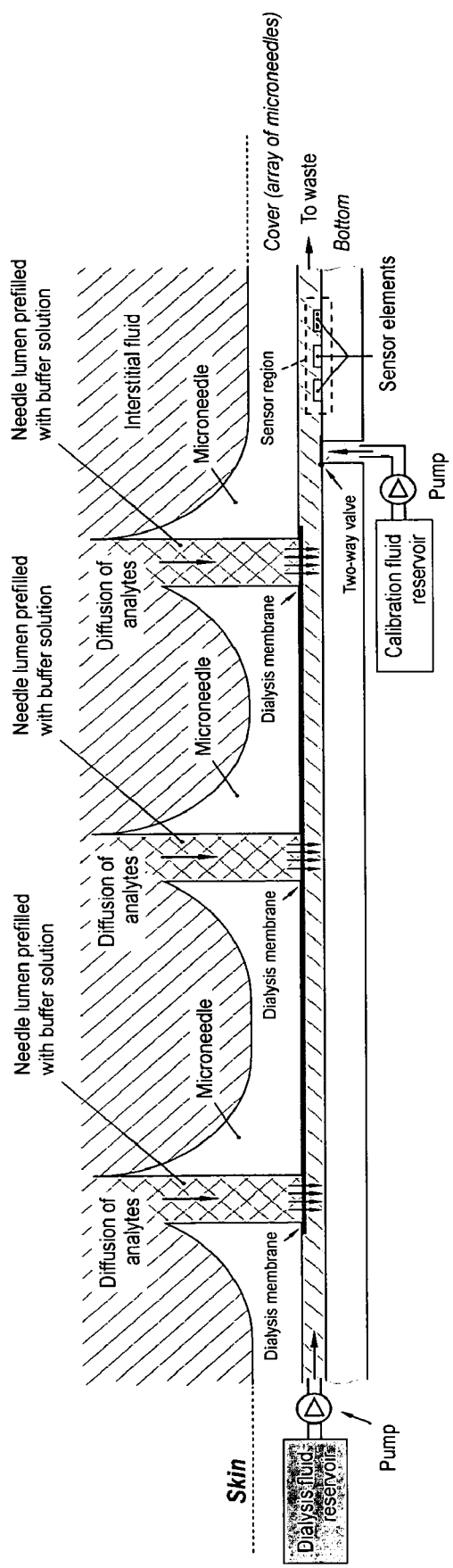
FIG. 4 illustrates an example schematic diagram of a sensor system showing three representative microneedles, a dialysis membrane, fluid reservoirs and pumps, according to specific embodiments of the present invention.

FIG. 4 illustrates an example schematic diagram of a sensor system showing three representative microneedles, a dialysis membrane, fluid reservoirs and pumps, according to specific embodiments of the present invention. In this example system, separate calibration and dialysis fluids reservoirs are used, with two micropumps and valves as shown.

EXAMPLE 4

Microneedle with Cross-linked Polymer

Figure 5:
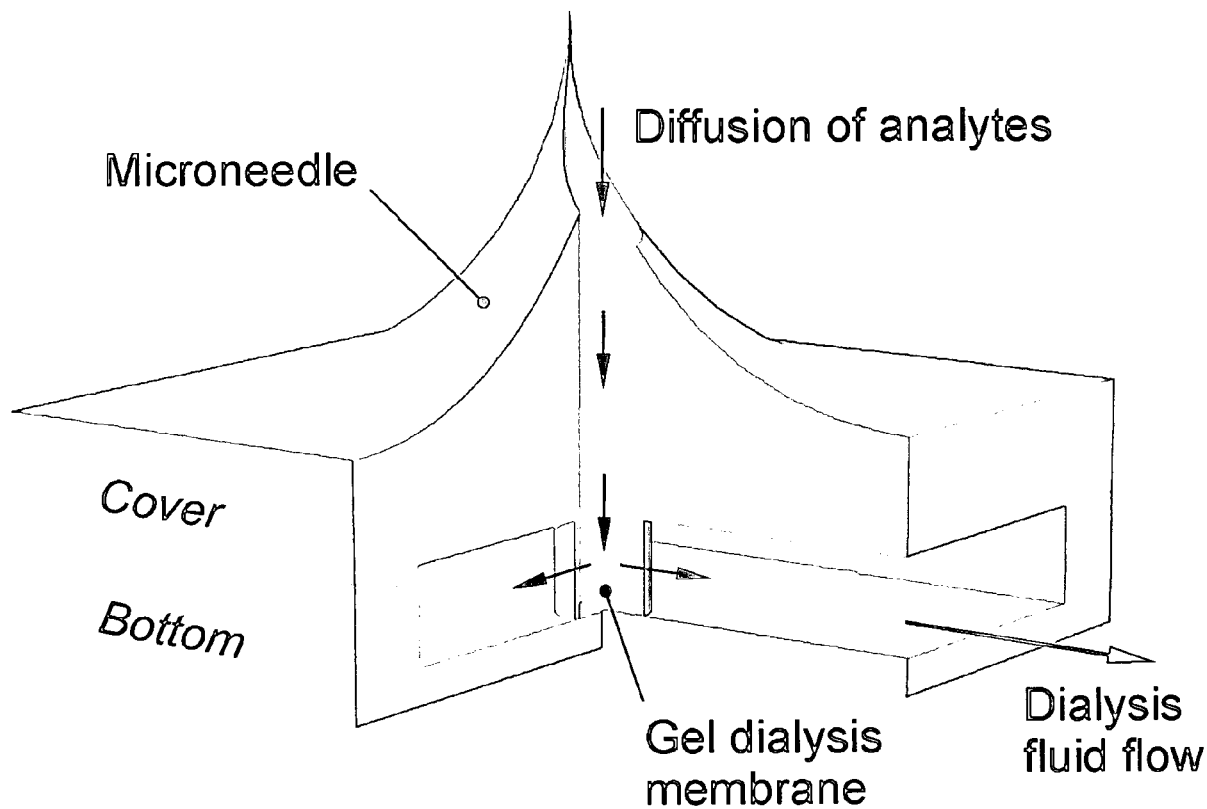
FIG. 5 illustrates an example microneedle component with a crosslinked polymer used as a dialysis membrane and an active membrane optionally with immobilized enzymes according to specific embodiments of the invention.

FIG. 5 illustrates an example microneedle component with a crosslinked polymer used as a dialysis membrane and an active membrane optionally with immobilized enzymes according to specific embodiments of the invention. In a particular example construction, the polymer is crosslinked in the flow channel right underneath the needles where it forms walls around the needle lumen opening from the bottom to the top of this channel. In this configuration, the compounds from the interstitial fluid diffuse through the needle lumen and through the gel wall where they might undergo enzymatic reactions before getting into the dialysis fluid in the case where enzymes have been immobilized in this membrane.

Thus, in this specific example, locally crosslinked polymer forms walls in the flow channel underneath the needles, separating the interstitial fluid from the dialysis fluid. Analytes can diffuse through this polymer.

Electrical Components

Figure 6:
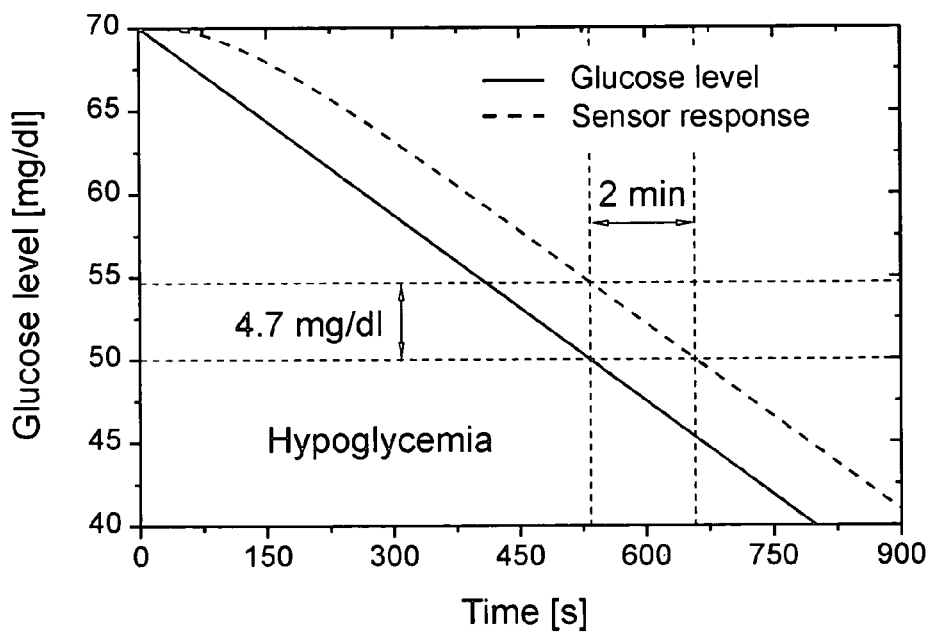
FIG. 6 illustrates an example sensor response to a fast decreasing glucose level (2.25 mg/dl/min) showing that the time lag of the sensor response is approximately 2 min and thus, a hypoglycemia alarm could be triggered at 54.7 mg/dl according to specific embodiments of the invention.

A prototype system using the glucose as describe above was tested. FIG. 6 illustrates an example sensor response to a fast decreasing glucose level (2.25 mg/dl/min) showing that the time lag of the sensor response is approximately 2 min and thus, a hypoglycemia alarm could be triggered at 54.7 mg/dl according to specific embodiments of the invention.

Figure 7:
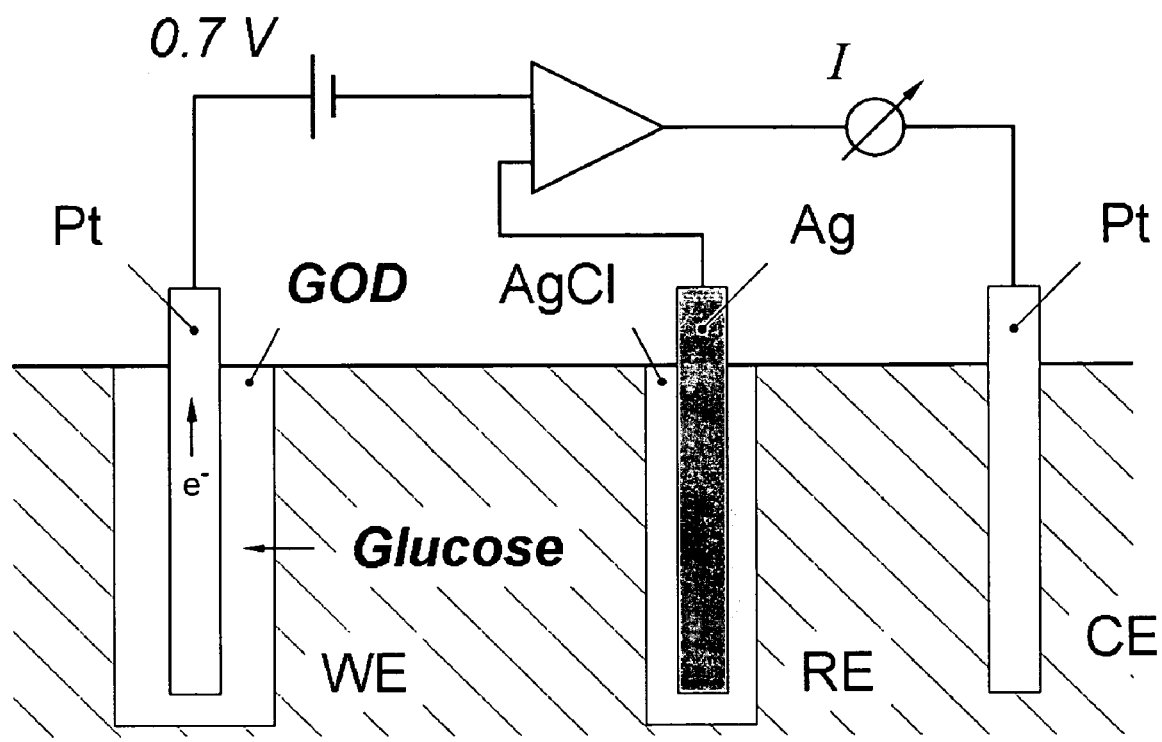
FIG. 7 illustrates the electrical operation of an example enzyme-based electrochemical glucose sensor that can be used in systems and/or devices according to specific embodiments of the invention.

FIG. 7 illustrates the electrical operation of an example enzyme-based electrochemical glucose sensor that can be used in systems and/or devices according to specific embodiments of the invention. Another example glucose sensor is an integrated glucose sensor as discussed in M. Lambrechts and W. Sansen, Biosensors: Microelectrochemical devices, IOP Publishing, New York, 1992. Other sensor technology can be employed according to specific embodiments of the invention.

Figure 8:
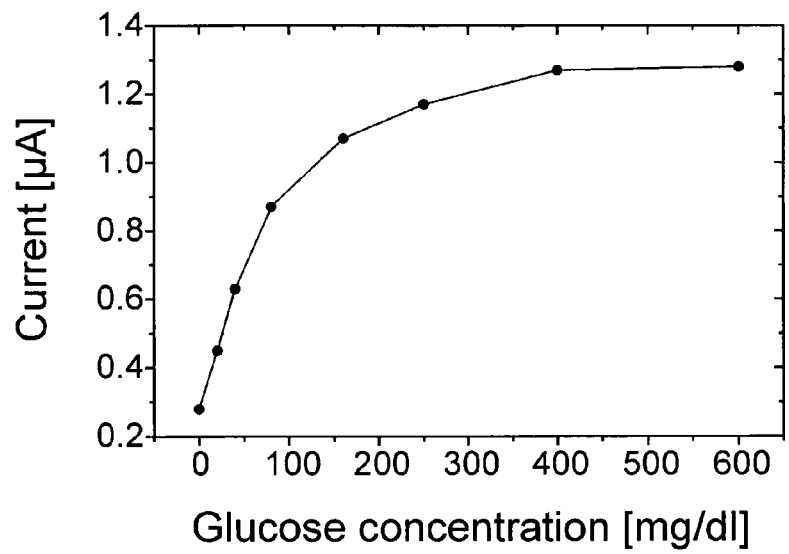
FIG. 8 illustrates an example of data showing sensor calibration (left) according to specific embodiments of the present invention.

FIG. 8 illustrates an example of data showing sensor calibration (left) according to specific embodiments of the present invention.

In specific example systems, power supply and signal processing are achieved with a portable pager size device that connects to the microsystem. The portable pager sized external device can also include components for connecting to a computer and/or information processing system, either through a physical adaptor or wireless connection. A wireless connected device can be used in home and or office settings to allow an individual to be remotely monitored by, for example, a health care provider or elder care provider. A large number of such monitoring devices can be used in institutional settings, such as care facilities and/or work environments and/or hospitals to monitor a number of individuals.

Micropumps

Techniques and/or devices for constructing micropumps are well-known in the art and in general any micropumping technique can be included in systems according to specific embodiments of the invention. Example micropumps that can be used according to specific embodiments of the invention are discussed in N.-T. Nguyen, X. Huang, T. K. Chuan, MEMS-Micropumps: A Review, Journal of fluids Engineering, Vol. 124, 2002.

Valve

According to specific embodiments of the invention, a two-way valve consisting of a diffusion barrier and a check valve allow pumping either dialysis fluid or calibration fluid to the sensor is employed. This valve represents a novel design. Other valve designs can be incorporated in specific embodiments of the invention. It should be understood that a the diffusion barrier as illustrated in FIG. 3 is schematically shown perpendicular to a substrate in order to illustrate its construction. In specific embodiments, this barrier will be constructed in a plane parallel to the largest substrate plane.

Integrated Systems

Figure 9:
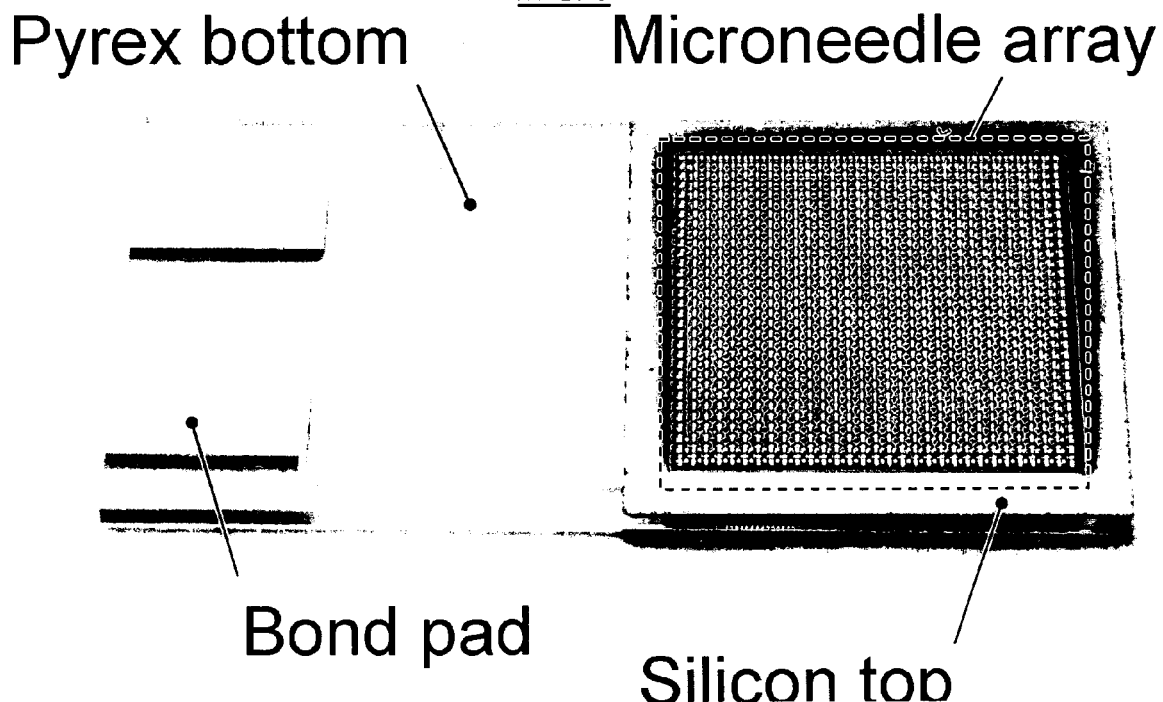
FIG. 9 illustrates an example device with approximately 1000 microneedles and other components according to specific embodiments of the present invention.

An example embodiment was fabricated using fabrication steps that will be familiar in the art in addition to the teachings provided herein and in cited references. FIG. 9 illustrates an example device with approximately 1000 microneedles and other components according to specific embodiments of the present invention. Other processes, including processing having printing, molecular growth and/or other fabrication steps as understood in the art can also be used to fabricate a device embodying the invention. Thus, FIG. 9 can also be understood as illustrating an early prototype of a simplified monitor, which only consists of out-of-plane microneedles and a glucose sensor.

5. Microneedle Designs

A number of different methods are known for forming microneedles and a variety of these methods and different types of microneedle arrays can be used in a device according to specific embodiments of the invention. One such device is described in B. Stoeber, D. Liepmann, Method of Forming Vertical, Hollow Needles within a Semiconductor Substrate, and Needles Formed thereby, U.S. Pat. No. 6,406,638, Jun. 18, 2002. Microneedle arrays built using plastic and metal technology can also be used in a device according to specific embodiments of the invention.

Figure 10:
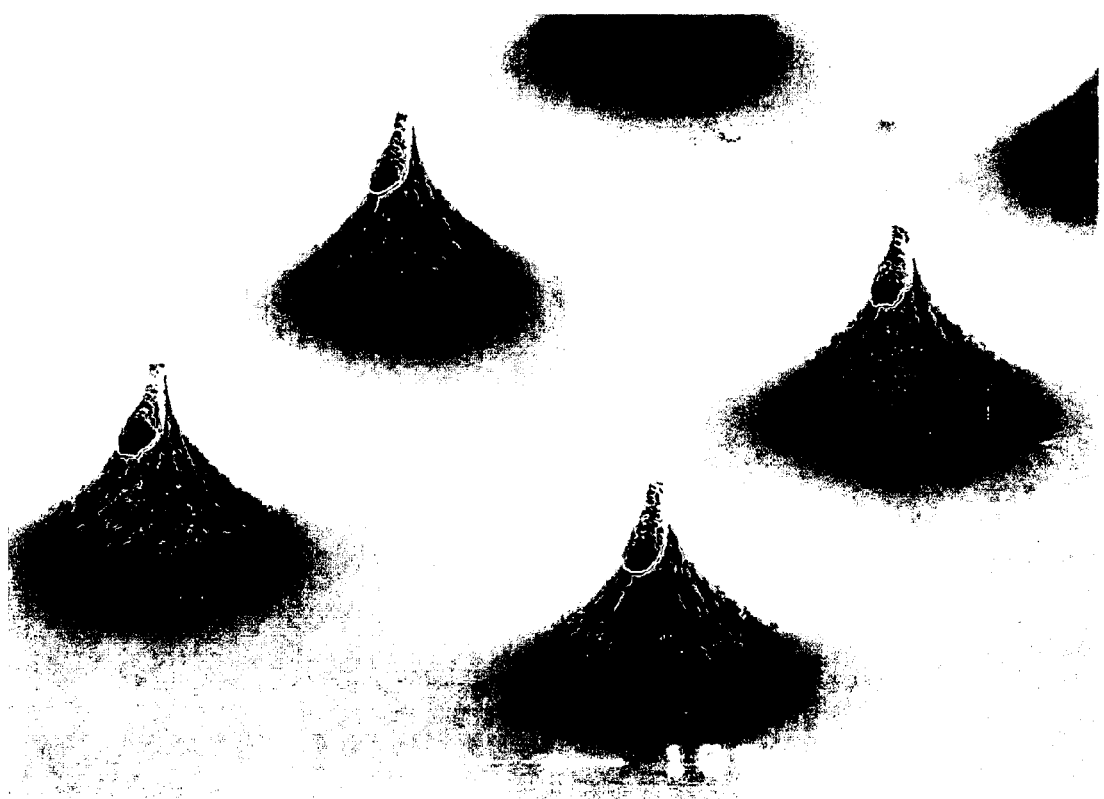
FIG. 10 is a scanning electron micrograph showing an example microneedle configuration of one configuration according to specific embodiments of the invention.

FIG. 10 is a scanning electron micrograph showing an example microneedle configuration of one configuration according to specific embodiments of the invention. These microneedles can be used in specific embodiments of the invention and can fabricated as discussed in U.S. Pat. No. 6,406,638.

Figure 11:
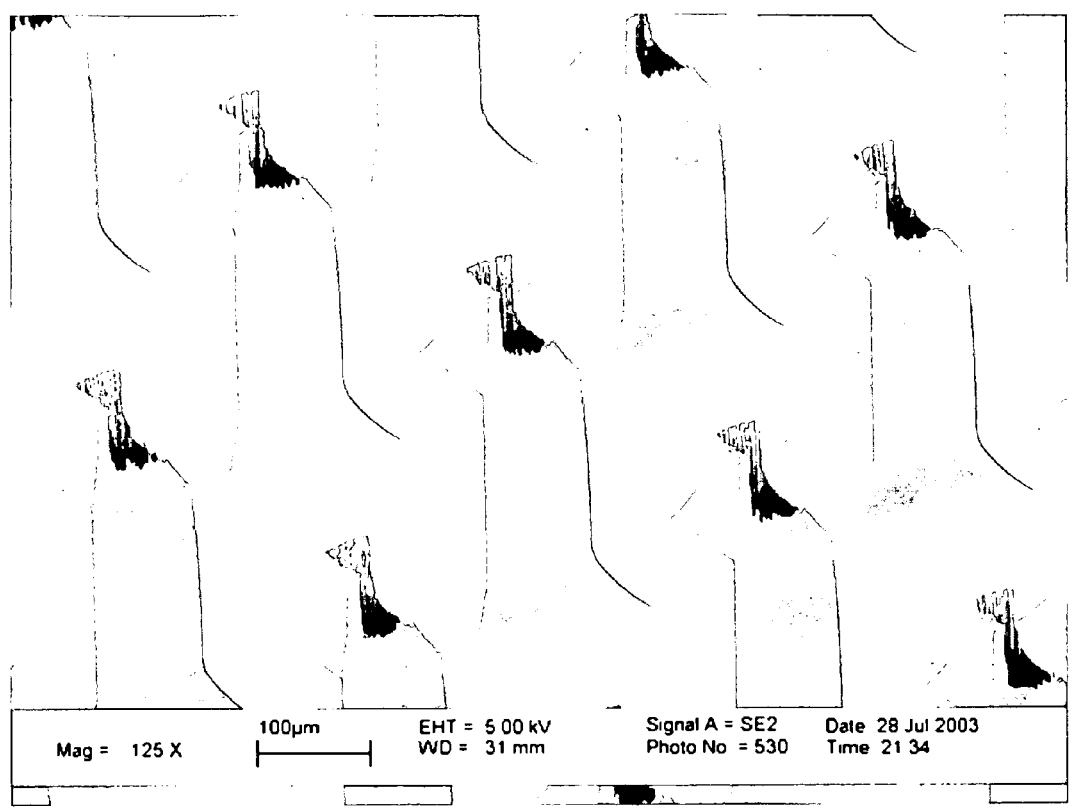
FIG. 11 is a scanning electron micrograph showing an example of an alternative microneedles configuration (e.g., needles are approximately 270 μm long, 100 μm wide shaft, ID=50 μm, 400 μm pitch) that can be used in a dialysis system according to specific embodiments of the invention.

It has been found is some situations, however, that longer and/or sharper microneedles may provide more easy penetration of various surfaces. FIG. 11 is a scanning electron micrograph showing an example of an alternative microneedles configuration (e.g., needles are approximately 270 µm long, 100 µm wide shaft, ID=50 µm, 400 µm pitch) that can be used in a dialysis system according to specific embodiments of the invention. These needles can be fabricated using the etching techniques disclosed in U.S. Pat. No. 6,406,638, but with etching steps modified to achieve longer and/or sharper needles. This new microneedle design allows easier penetration of the skin due to a longer needle shaft, which causes the skin to stretch more and to break the stratum corneum. In some cases, these longer microneedles may reach the capillary bed of the dermis so that blood is sampled through the needles along with or instead of interstitial fluid.

While etched microneedle designs have been the most studied so far, other methods for forming microneedles can also be employed according to specific embodiments of the invention.

In one such method, a liquid such as a polymeric fluid can be poured onto a surface with thin pillars perpendicular to this surface. Different mechanisms can then be used to make this liquid higher around the pins than further away from them to generate the needle shape and the pins can then be removed after or during hardening of the liquid. The liquid could either be poured onto the molding surface from the top, it could enter from the side, or it could be pushed onto this surface through bottom holes in this surface. It is also possible to condensate or to sublime this material on the molding surface. Capillary action can cause the liquid to rise up on the surface of the thin pillars, with the height of rise will depend on the contact angle between the fluid and the pillars, the surface tension of the fluid and its specific weight. The liquid can then be hardened in its current conformation.

6. Breaking Outer Surface or Membrane

In further embodiments, the invention involves a novel method for breaking the outer layer of mammalian skin (stratum corneum) in order to create an interface with bodily fluids. This method consists of applying a localized high pressure-load to one or multiple small location on the skin in order to yield the outer skin layer. This effect can be promoted by applying a preload to the skin in form of lateral stretching.

Large hypodermic needles are classic means for the penetration of mammalian skin. This method has been used for injection as well as extraction of fluids from organisms. It requires sharp individual needles, usually made from steel, which cut through the outer skin layer and open a passage for insertion of the needle shaft into the tissue. Some proposed microneedle methods replicate this method on a smaller scale, where needle shaft lengths were typically less that 1 mm. The target depth in the tissue is typically not as deep as in the case of hypodermic needles. It typically ranges from tens to only hundreds of microns.

Effort has been spent on generating extremely sharp microneedles, which cut the skin open in order to allow injection of fluids into the organism or sampling of bodily fluids in the same fashion as in the case of hypodermic needles. However, fabrication of extremely sharp small needles can be difficult and expensive. Furthermore, it is unclear if the sharp tips of these microneedles have a sufficient mechanical strength to prevent breakage during usage. In addition, the skin and the underlying tissue are very flexible for small deflection as typically caused by short microneedles, so that the classical approach of cutting through the stratum corneum risks to fail due to insufficient contact pressure. This problem is even more severe in the case of needle arrays, where a distributed load over a wide area of skin can results in a bed of nails effect, which merely leads to uniformly pushing down the skin. Nevertheless, microneedles allow easy integration into advanced drug delivery systems or into systems for detection of body fluids and/or compounds in an organism, which could be very important for the future of medical care.

A number or alternative methods for skin penetration have been developed, which use high-speed impact of some material onto the skin. The skin cannot deform rapidly because of its inertia and ruptures. A. B. Baker and J. E. Sanders (Fluid mechanics analysis of a spring-loaded jet injector, IEEE Transactions on Biomedical Engineering, 46 (2), February 1999, pp. 235-242) used the inertial force of a thin liquid jet to cut through the skin, M. A. F. Kendall, P. J. Wrighton Smith and B. J. Bellhouse (Transdermal ballistic delivery of microparticles: Investigation into skin penetration, *Proceedings of the 22nd Annual EMBS International Conference*, July 23-28, Chicago, Ill., USA, pp. 1621-1624, 2000) and X. L. Yu, X. W. Zhang, Y. Wang, J. Xie and P. F. Hao (Particle acceleration for delivery deoxyribonucleic acid vaccine into skin in vivo, *Review of Scientific Instruments,* 72 (8), pp. 3390-3395, 2001) drove small ballistic particles through the outer skin layer into deeper tissue, and S. Lee, D. J. McAuliffe, T. Kodama and A. G. Doukas (In vivo transdermal delivery using a shock tube, *Shock Waves,* 10, pp. 307-311, 2000) generated shock waves in order to enhance drug diffusion into the skin. A more destructive method for opening the skin uses localized heat to burn a hole into the stratum corneum (M. Paranjape, J. Garra, S. Brida, T. Schneider, R. White, J. Currie, "Dermal thermo-poration with a PDMS-based patch for transdermal biomolecular detection", *Technical Digest of the Solid-State Sensor, Actuator, and Microsystems Workshop* 2002, Hilton Head Island, S.C., USA, June 2-6, pp. 73-76, 2002).

These results lead to the conclusion that breaking the stratum corneum with shorter microneedles in order to provide diagnostic sensing may be improved by using a different mechanism than simply penetrating the stratum corneum with needles. The needle tips are rather used to generate high local stress in the stratum corneum without breaking it, while providing an additional load on the skin from a pressurized liquid inside the needles to rupture the skin.

Figure 12:
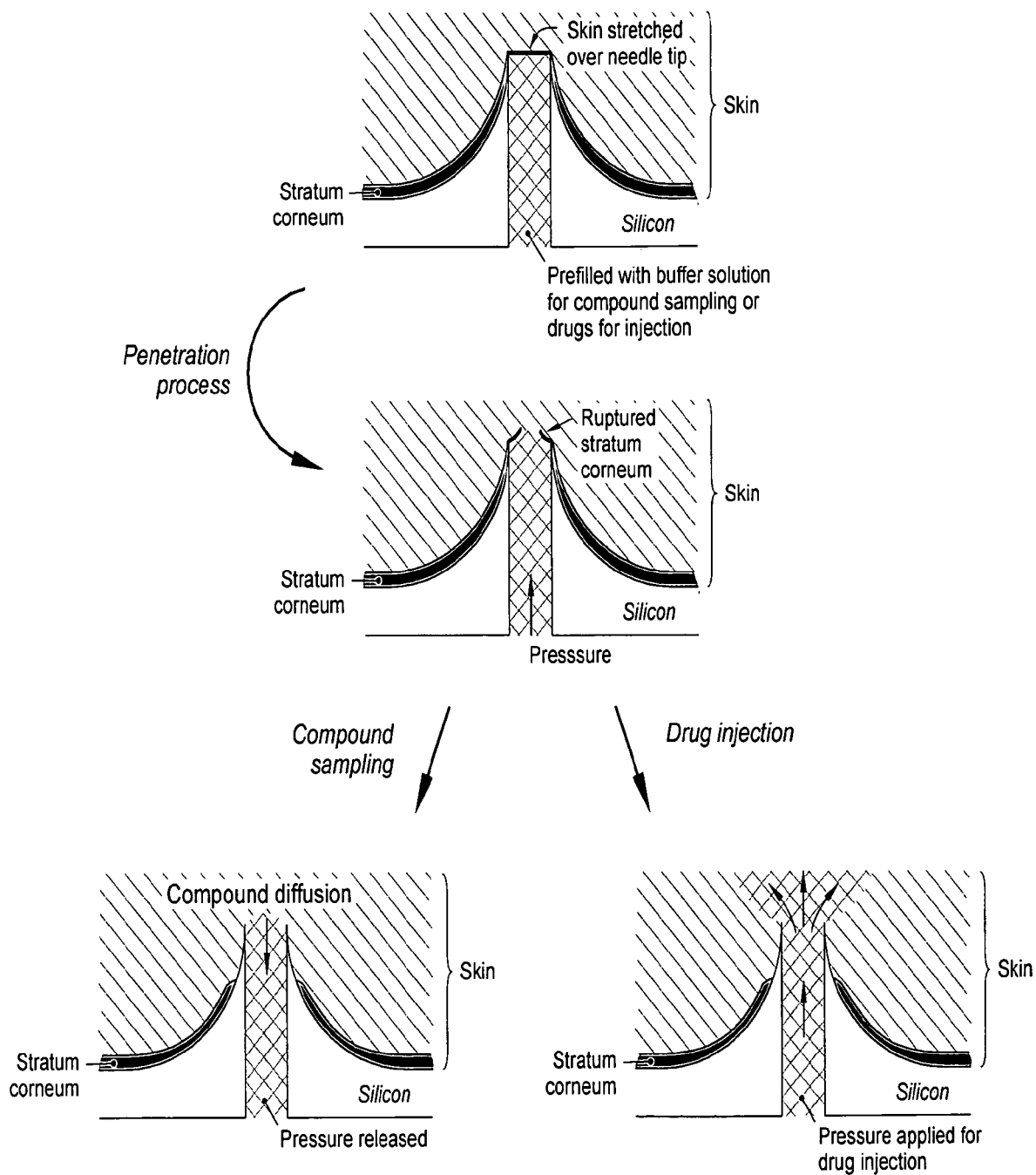
FIG. 12 is a schematic diagram of a skin penetration method using hollow out-of-plane microneedles according to specific embodiments of the invention.

This mechanism can be used for glucose sampling through the short microneedles. In this approach, the outer skin layer can be broken by applying high pressure to a small local skin region, which results in rupture of the cell matrix. This effect can be promoted by applying a preload to the skin in form of lateral stretching. Pressing such a microneedle against the skin as shown in FIG. 12 (top) stretches the skin over the needle tip, so that additional pressure applied to the fluid inside the needle lumen results in yielding of the skin, which ruptures and opens a passage way between fluids inside the needle lumen and bodily fluids underneath the broken skin layer, FIG. 12 (middle). The stratum corneum slips back while the needle tip is inserted into the epidermis.

This opened passage can be used for multiple purposes. Compounds or fluids from within the organism can get transported through the needle lumen by diffusion or other transport mechanisms as shown in FIG. 12 (bottom left), so that these compounds can be detected or quantified for monitoring purposes. Such compounds or fluids could be glucose, lactate, proteins, lipids, DNA, cells or blood.

This flow passage can also be used for injection of fluids into the organism as shown in FIG. 12 (bottom right). In addition, this interface with bodily fluids can be used to send and/or collect electrical or optical signals into or from the organism for detection purposes. Multiple needles in form of an array can be used simultaneously for an identical purpose or multiple applications.

As a major advantage, this perforation method does not require extremely sharp microneedles, which allows simpler fabrication at low cost. Furthermore, less sharp microneedles are less susceptible to breakage of their tip increasing their reliability. In addition, the usage of less sharp needles is safer since they only penetrate skin in response to the combined forces of stretching the skin and pressurizing the fluid.

Figure 13:
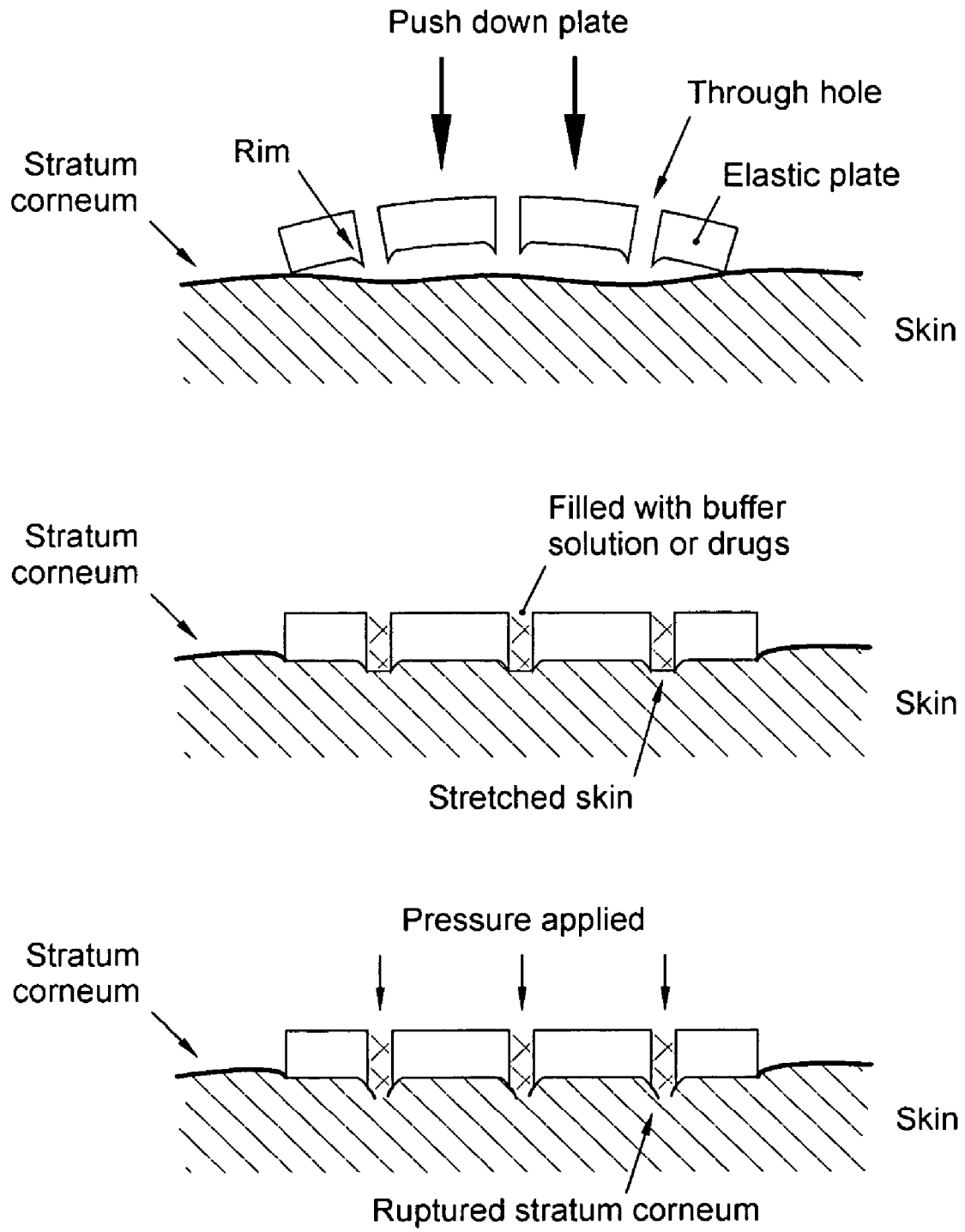
FIG. 13 is a schematic diagram of a skin penetration method using a pre-bent elastic plate with through holes according to specific embodiments of the invention.

In certain cases it might be possible to apply this method of skin perforation without using microneedles. FIG. 13 shows an apparatus that stretches the skin as it is being pressed against it. The base of this apparatus extends laterally while its edges hold on to the skin. This base also provides small trough holes, which can be used to apply additional pressure to the small regions of the skin underneath these holes by pressurizing a fluid from the side of the base opposite to the skin. Small rims around these openings on the side of the skin provide a good seal between the apparatus and the skin during pressure application.

7. Immobilization Technique

According to specific embodiments of the invention, wafer-level fabrication of an integrated system of the invention is preferably performed using anodic bonding at relatively high temperatures, such as above about 100° C. However, enzymes or substances of interest in integrated systems according to specific embodiments of the invention and in other BioMEMS and similar systems can be adversely affected at maximum temperatures well below this temperature. Glucose oxidase, for example, denatures at temperatures above 60° C.

Thus, in specific embodiments, the present invention involves a novel immobilization technique that allows patterning inside microchannels after bonding or other high-temperature steps have been performed. This technique is applicable in various applications, such as other BioMEMS that require high temperature steps and the integration of heat-sensitive bioactive materials.

Figure 14A:
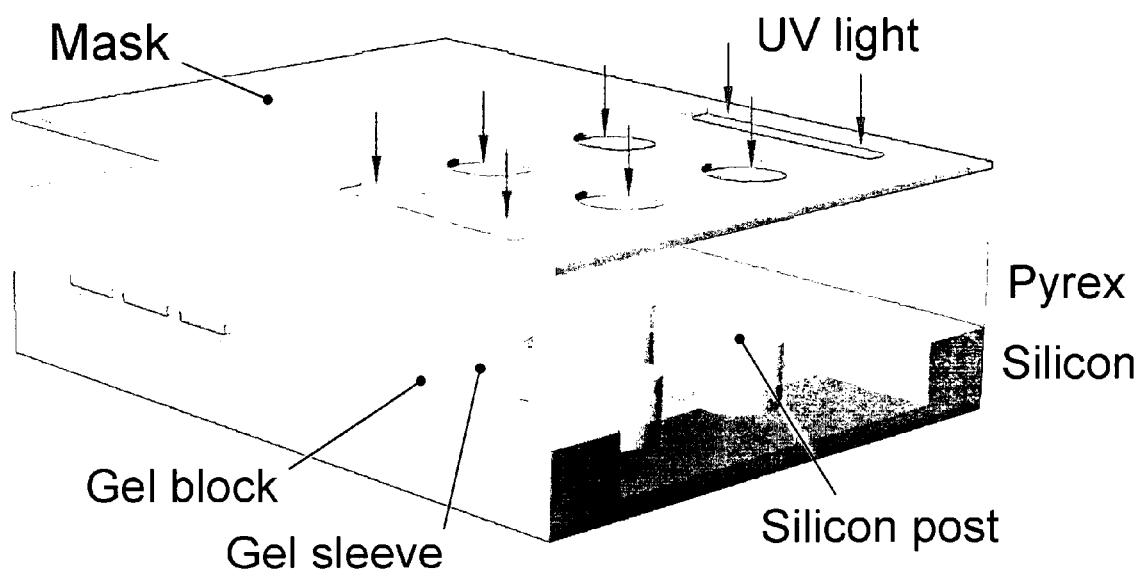
FIG. 14 illustrates aspects of a novel technique for in-device enzyme immobilization which in this particular example is based on poly(vinyl alcohol)-styrylpyridinium, a water-soluble photosensitive polymer containing enzymes according to specific embodiments of the present invention. The figure can be understood to illustrate an sensor/dialysis portion of a sensor system to which a microneedle array may be attached.
Figure 14B:
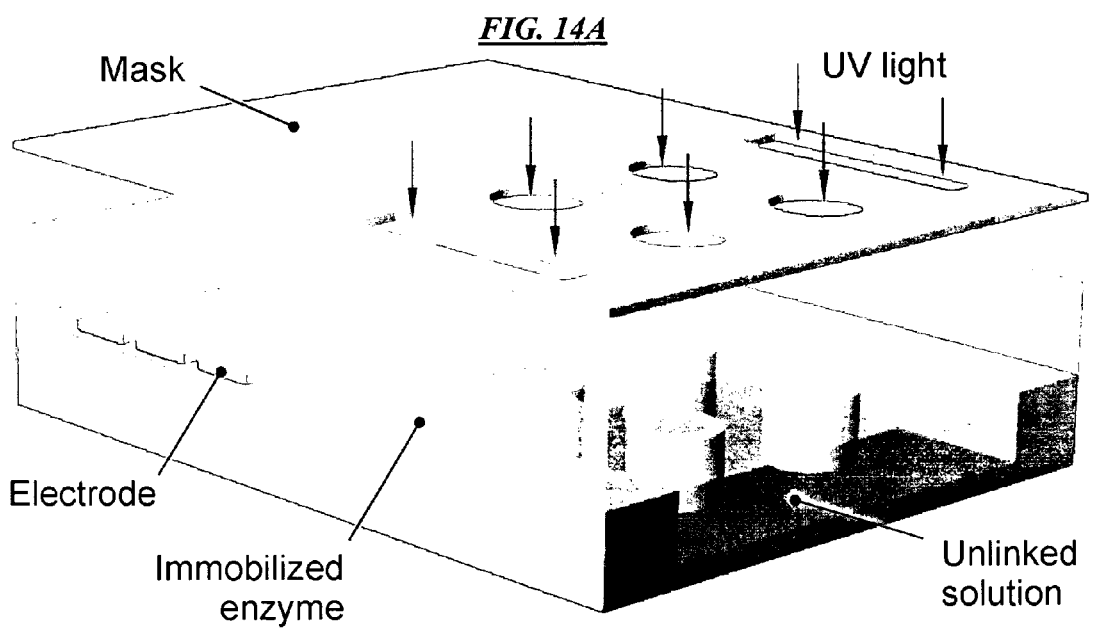

FIG. 14 illustrates aspects of a novel technique for in-device enzyme immobilization which in this particular example is based on poly(vinyl alcohol)-styrylpyridinium, a water-soluble photosensitive polymer containing enzymes according to specific embodiments of the present invention. According to specific embodiments of the invention, an in-device enzyme immobilization technique uses a photosensitive water-soluble polymer, such as, for example, PVA-SbQ for example as discussed in K. Ichimura, *A Convenient Photochemical Method to Immobilize Enzymes*, Journal of Polymer Science: Polymer Chemistry Edition, John Wiley & Sons, Vol. 22, pp. 2817-2828, (1984). This polymer is generally is mixed with buffer solution (e.g., PBS, pH 7.4) containing a substance of interest to be immobilized, such as glucose oxidase.

Basic example fabrication steps can be understood as follows: (1) High-temperature wafer bonding (e.g., Pyrex to silicon) and any other high-temperature steps are performed; (2) Channels are filled with enzyme-polymer solution, and (3) crosslinking polymer under UV light or other energy source to form gels in which, optionally, enzymes are entrapped; (4) rinsing out unlinked solution.

Figure 15A:
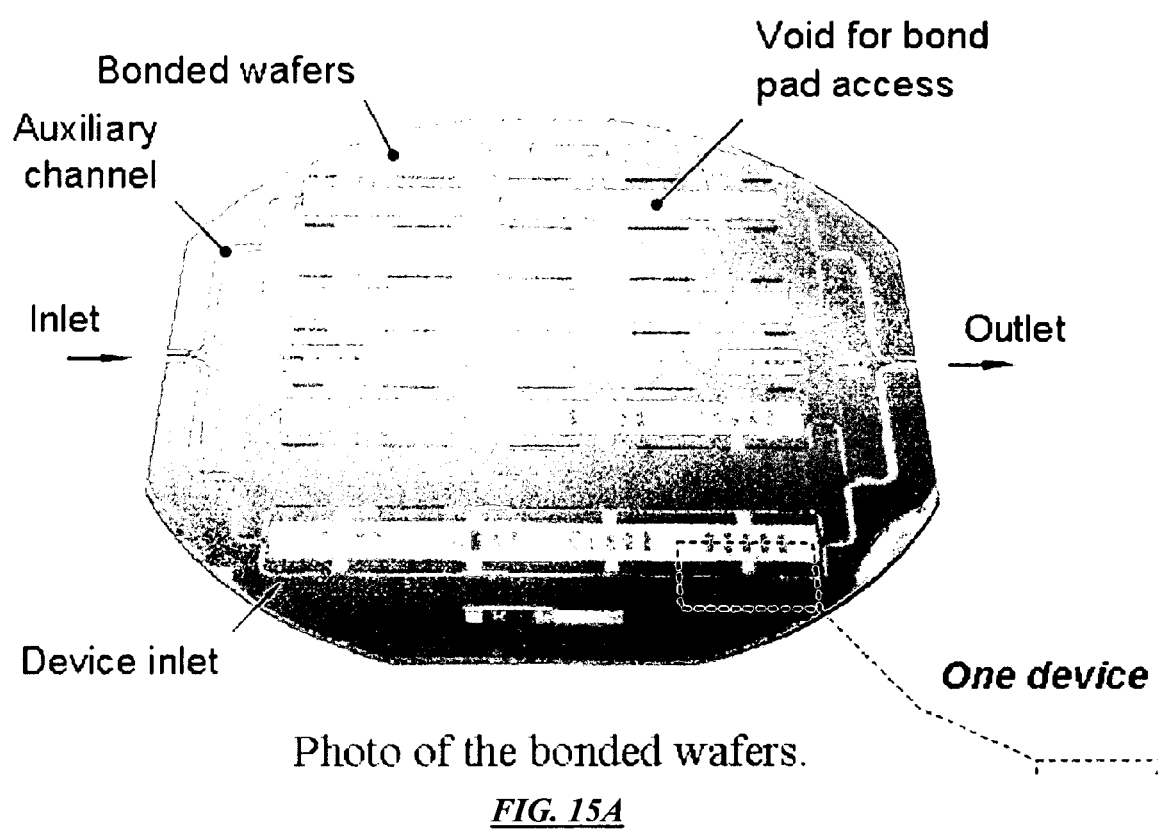
FIG. 15A-B illustrates an example wafer stack with auxiliary channels for filling according to specific embodiments of the present invention.
Figure 15B:
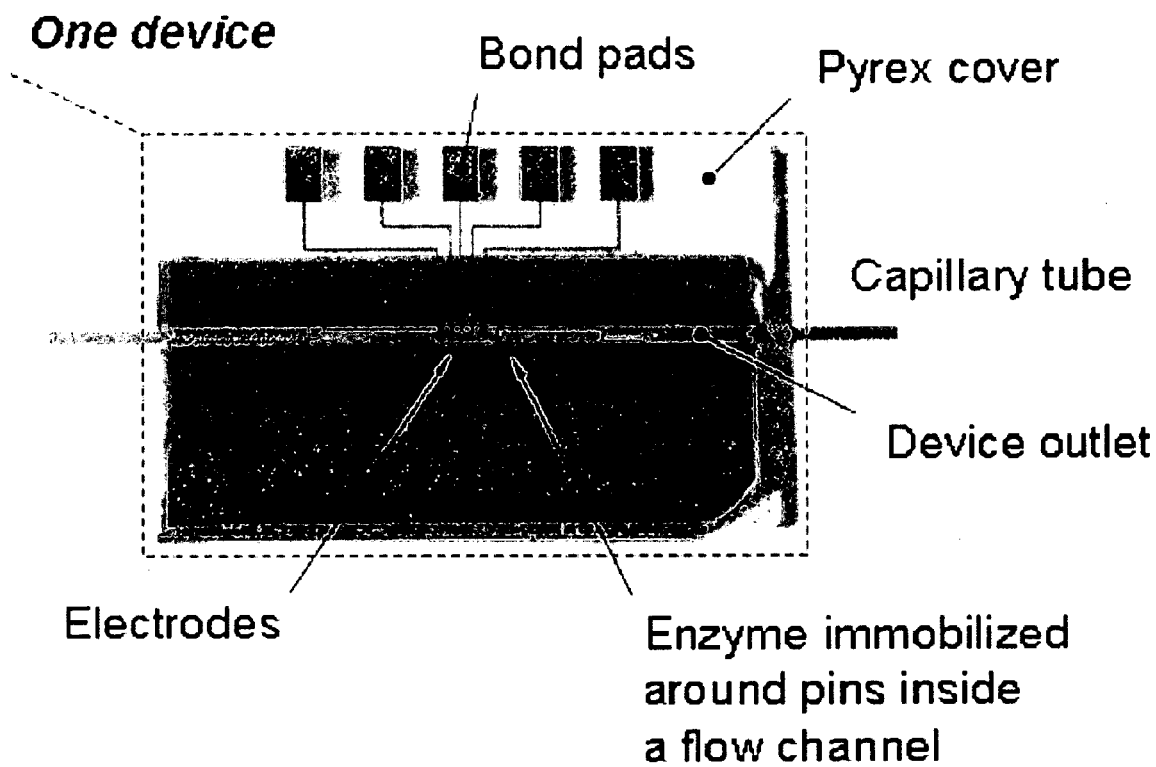

More specifically, after high temperature processing and/or fabrication steps (such as, anodic wafer bonding of a Pyrex cover and silicon base) areas and/or devices can be filled with this substance-polymer solution. In particular embodiments, auxiliary channels can be used connecting all regions of interest and thereby allowing filling of an entire wafer or large area thereof by capillary force through a single inlet in a short time and generally without bubble formation. FIG. 15A-B illustrates an example wafer stack with auxiliary channels for filling according to specific embodiments of the present invention.

In further embodiments, the polymer is selectively exposed to UV light (e.g., at 365 nm (600 mJ/cm$^2$)) optionally through a transparent or partially transparent material (e.g., a Pyrex cover) generally using a shadow mask to cover those areas where it is not desired to fix the substance. Thus, the substance of interest (e.g., an enzyme) is entrapped in locally formed gel regions. In a specific example embodiments, the low absorption of Pyrex at 365 nm makes an exposure through the glass cover possible. However a variety of different materials can be used with different wavelengths of light depending on the wavelength having the desired effect on the chosen polymer solution. Many combinations of transparency and useable polymer materials and light wavelengths can be used in different embodiments of the invention and the selection of a workable combination of these will be within the ordinary skill of those in the art having benefit of this disclosure.

When desired during fabrication (e.g., after wafer dicing), the unlinked enzyme-polymer solution can be rinsed out of the chips by soaking them in buffer solution for several hours.

Figure 16:
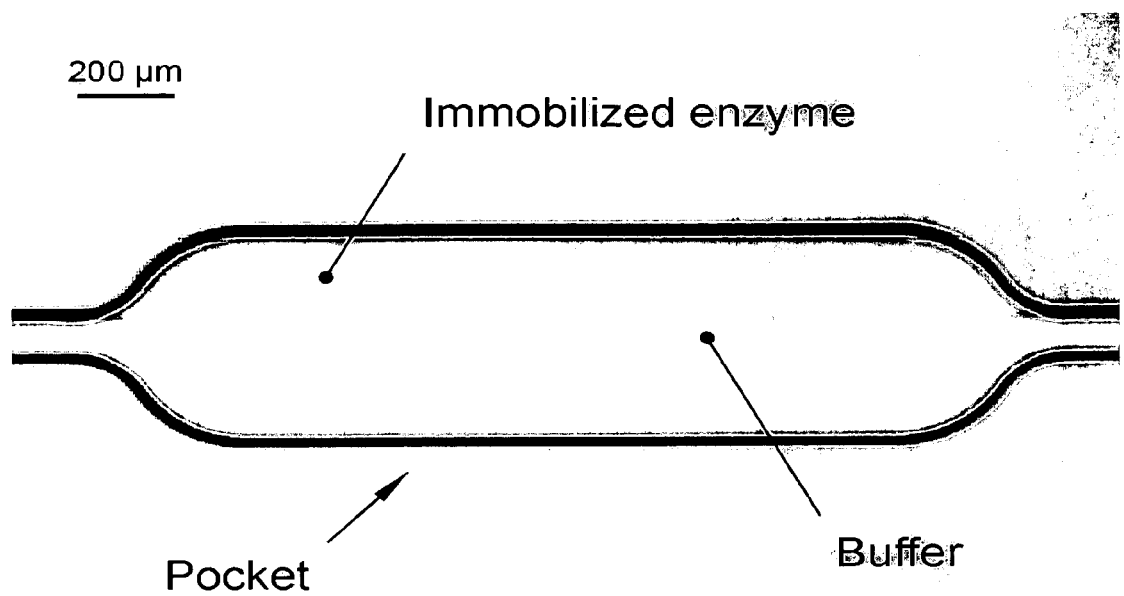
FIG. 16 illustrates an immobilized heat-sensitive substance in side pockets of a flow channel according to specific embodiments of the present invention.
Figure 17:
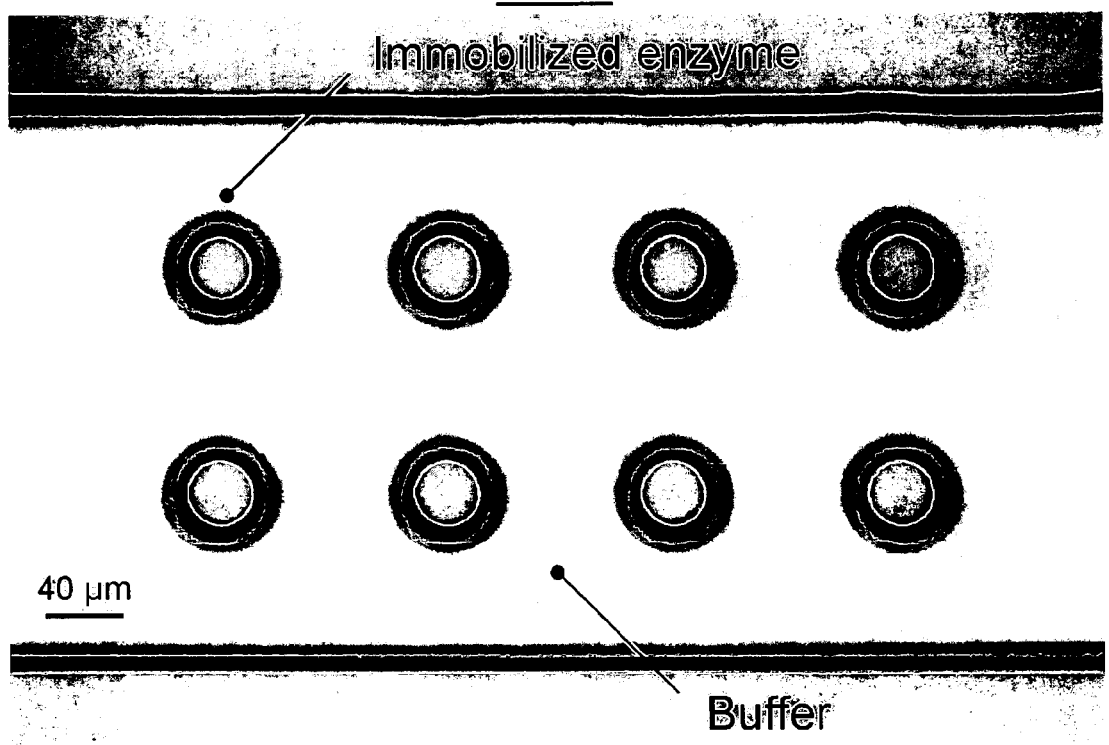
FIG. 17 illustrates an immobilized heat-sensitive substance around pins inside a flow channel according to specific embodiments of the present invention.

Experiments using specific example embodiments show that the enzyme activity remains constant, which means that only a negligible amount of enzyme is washed out of the gel while soaking. Furthermore an example tested gel does not swell and thus will not block the flow channel during sensor operation when dialysis fluid flows through the sensor. In particular embodiments, maintenance of the gel in place is aided by crosslinking it in side pockets or around pins inside the channel, an example of which is shown in FIG. 16 and FIG. 17. This assists the gel to be held in place during operation. Other techniques to enhance gel-adhesion can be used, such as modifying the surface to which the gel should adhere, either mechanically (e.g., by introducing roughness in the surface, etc.) or chemically by changing the chemical properties of the gel or change the properties of the material and/or surface to which the gel should adhere.

In further embodiments, dicing the wafer stack into chips opens the in-plane fluid ports of each sensor device. Capillary tubes (∅=360 μm) can be glued into the fluid ports. Furthermore, Side pockets or pins (anchors) inside the flow channels can be used to hold the gel in place when dialysis fluid (buffer) flows through the channels during sensor operation.

In a specific example embodiment related to glucose detection as elsewhere described herein, in order to show that glucose oxidase is suitable for photochemical immobilization the effect of UV light (365 nm) on the enzyme activity has been investigated. No significant decrease in activity could be measured for exposure energies up to 18000 mJ/cm$^2$. Thus glucose oxidase is very insensitive to UV light and the exposure energy of 600 mJ/cm$^2$ use to crosslink PVA-SbQ has no effect on the enzyme activity. In addition the enzyme can preserve its activity since it is only entrapped inside the gel and not crosslinked to it.

However, in specific embodiments, the effective activity of the immobilized enzyme is reduced compared to enzyme in solution due to the diffusion limited glucose concentration inside the gel. For example, it has been found that the effective activity of enzyme immobilized in a 1.5 mm thick gel layer with a free surface of 40 mm$^2$ and 0.006 U glucose oxidase drops by 70% compared to 0.006 U of free enzyme in buffer solution for the same pH value and the same glucose concentration of 90 mM. Such activity loss can be compensated by a suitable sensor design, which guarantees a thin gel film with a large free surface area. Furthermore a high enzyme concentration is required in the gel to ensure a diffusion controlled amperometric current independent of the enzyme activity. However, a large amount of enzyme results in an oxygen-limited current at higher glucose concentrations. For a thin film of 5 μl gel containing 0.025 U glucose oxidase the current approaches saturation at a glucose concentration of about 180 mg/dl In further embodiments, the invention can be embodied in advanced enzyme-based BioMEMS, such as a continuous self-calibrating glucose monitor. In specific embodiments, the enzyme is immobilized as discussed above in a micro-scale flow channel. As will be understood from the above, wafer-level fabrication of such BioMEMS with integrated fluidic components can require bonding techniques at elevated temperatures such as anodic bonding. This conflicts with the high sensitivity of enzymes to temperature. Glucose oxidase, for instance, starts to denature at a temperature of about 60° C. Thus, enzyme immobilization needs to be performed after wafer bonding.

8. Diagnostic Uses

As described above, following identification and validation of a sensor for a particular substance, including biological molecules such as sugars, proteins, fats, or any substance of interest according to the invention, in specific embodiments such detectors are used in clinical or research settings, such as to predictively categorize subjects into disease-relevant classes, to monitor subjects on a continuous basis to detect a substance of interest, etc. Detectors according to the methods the invention can be utilized for a variety of purposes by researchers, physicians, healthcare workers, hospitals, laboratories, patients, companies and other institutions. For example, the detectors can be applied to: diagnose disease; assess severity of disease; predict future occurrence of disease; predict future complications of disease; determine disease prognosis; evaluate the patient's risk; assess response to current drug therapy; assess response to current non-pharmacologic therapy; determine the most appropriate medication or treatment for the patient; and determine most appropriate additional diagnostic testing for the patient, among other clinically and epidemiologically relevant applications. Essentially any disease, condition, or status for which a substance or difference can be detected in an interstitial fluid can be evaluated, e.g., diagnosed, monitored, etc. using the diagnostic methods of the invention, see, e.g. Table 1.

In addition to assessing health status at an individual level, the methods and diagnostic sensors of the present invention are suitable for evaluating subjects at a "population level," e.g., for epidemiological studies, or for population screening for a condition or disease.

Web Site Embodiment

The methods of this invention can be implemented in a localized or distributed data environment. For example, in one embodiment featuring a localized computing environment, a sensor according to specific embodiments of the present invention is configured in proximity to a detector, which is, in turn, linked to a computational device equipped with user input and output features. In a distributed environment, the methods can be implemented on a single computer, a computer with multiple processes or, alternatively, on multiple computers. Sensors according to specific embodiments of the present invention can be placed onto wireless integrated circuit devices and such wireless devices can return data to a configured information processing system for receiving such devices. Such devices could, for example, be configured to be affixed to a subject's body.

Kits

A detector according to specific embodiments of the present invention is optionally provided to a user as a kit. Typically, a kit of the invention contains one or more sensors constructed according to the methods described herein. Most often, the kit contains a diagnostic sensor packaged in a suitable container. The kit optionally further comprises an instruction set or user manual detailing preferred methods of using the kit components for sensing a substance of interest.

When used according to the instructions, the kit enables the user to identify disease or condition specific substances (such as sugars and/or fats and/or proteins and/or anti-gens) using patient tissues, including, but not limited to interstitial fluids. The kit can also allow the user to access a central database server that receives and provides information to the user. Additionally, or alternatively, the kit allows the user, e.g., a health care practitioner, clinical laboratory, or researcher, to determine the probability that an individual belongs to a clinically relevant class of subjects (diagnostic or otherwise).

Embodiment in a Programmed Information Appliance

The invention may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

Integrated Systems

Integrated systems for the collection and analysis of detection results, including detection or expression profiles, molecular signatures, as well as for the compilation, storage and access of the databases of the invention, typically include a digital computer with software including an instruction set for sequence searching and/or analysis, and, optionally, one or more of high-throughput sample control software, image analysis software, data interpretation software, a robotic control armature for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system further comprises an electronic signal generator and detection scanner for probing a microarray. The scanner can interface with analysis software to provide a measurement of the presence or intensity of the hybridized and/or bound suspected ligand.

Readily available computational hardware resources using standard operating systems can be employed and modified according to the teachings provided herein, e.g., a PC (Intel x86 or Pentium chip—compatible DOS,™ OS2,™ WINDOWS,™ LINUX, or Macintosh, Sun or PCs will suffice) for use in the integrated systems of the invention. Current art in software technology is adequate to allow implementation of the methods taught herein on a computer system. Thus, in specific embodiments, the present invention can comprise a set of logic instructions (either software, or hardware encoded instructions) for performing one or more of the methods as taught herein. For example, software for providing the described data and/or statistical analysis can be constructed by one of skill using a standard programming language such as Visual Basic, Fortran, Basic, Java, or the like. Such software can also be constructed utilizing a variety of statistical programming languages, toolkits, or libraries.

FIG. 18 is a block diagram showing a representative example logic device in which various aspects of the present invention may be embodied. FIG. 18 shows an information appliance (or digital device) 700 that may be-understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

Various programming methods and algorithms, including genetic algorithms and neural networks, can be used to perform aspects of the data collection, correlation, and storage functions, as well as other desirable functions, as described herein. In addition, digital or analog systems such as digital or analog computer systems can control a variety of other functions such as the display and/or control of input and output files. Software for performing the electrical analysis methods of the invention are also included in the computer systems of the invention.

Thus, a microneedle-based system according to specific embodiments of the invention can be employed as an effective glucose monitor using a microneedle array and dialysis. Due to the optimum needle dimensions, it is sufficient to simply press the system onto the skin in order to reach the desired location in the epidermis with an abundant amount of interstitial fluid. The nerve endings are located deeper in the skin so that this procedure is painless. The glucose monitor can be attached to a skin location (for example, with a self-adhesive, medical tape, a band, etc.) by the patient himself without an assisted insertion procedure.

Other Embodiments

Although the present invention has been described in terms of various specific embodiments, it is not intended that the invention be limited to these embodiments. Modification within the spirit of the invention will be apparent to those skilled in the art. It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this submission, including any references filed as part of an Information Disclosure Statement, are incorporated by reference in their entirety.

What is claimed:

1. A method of monitoring glucose disorders comprising:
preparing a plurality of out-of-plane microneedles for applying to the skin of a subject with a dialysis membrane remaining outside the skin;
fixing a detecting substance useful in determining glucose levels on an opposite side of said dialysis membrane from said needles;
wherein said fixing is accomplished by placing a polymer-detecting substance solution at said opposite side of said membrane after higher temperature fabrication and/or assembly steps of said microneedles have been performed;
applying said plurality of out-of plane microneedles to the skin of a subject with a dialysis membrane remaining outside the skin; and
performing continuous glucose monitoring by testing composition of a dialysis fluid remaining outside the skin and separated from said microneedles by said dialysis membrane.

2. The method of claim 1 further comprising:
said microneedles comprising a plurality of dialysis membranes on a side opposite a side applied to said surface such that said membranes are not placed under said surface.

3. The method of claim 2 further wherein:
said plurality of dialysis membranes comprise a large total membrane surface that remains outside of said internal region.

4. The method of claim 1 further wherein:
a plurality of said microneedles are pre-filled with a fluid before said applying.

5. The method of claim 1 further wherein:
said microneedles are long enough to prestress a region of the surface at a needle lumen; and further comprising:
applying high pressure to a small local surface region through said microneedles to cause rupture of the cell matrix to open a connection between fluids inside a needle lumen and bodily fluids underneath the broken skin layer; and
using said connection to sample one or more substances of interest at and/or just below said surface.

* * * * *